(12) United States Patent
Bass et al.

(10) Patent No.: US 6,994,999 B1
(45) Date of Patent: Feb. 7, 2006

(54) ISOLATED DNA MOLECULE COMPRISING THE PROMOTER SEQUENCE OF A BOVINE MYOSTATIN GENE

(75) Inventors: James J. Bass, Hamilton (NZ); Ferenc Jeanplong, Chartwell (NZ); Ravi Kambadur, Hamilton (NZ); Mridula Sharma, Hamilton (NZ)

(73) Assignee: Ovita Limited, Dunedin (NZ)

( * ) Notice: Subject to any disclaimer, the term of this patent is extended or adjusted under 35 U.S.C. 154(b) by 0 days.

(21) Appl. No.: 09/743,312

(22) PCT Filed: Jul. 7, 1999

(86) PCT No.: PCT/NZ99/00107

§ 371 (c)(1),
(2), (4) Date: May 7, 2001

(87) PCT Pub. No.: WO00/01810

PCT Pub. Date: Jan. 13, 2000

(30) Foreign Application Priority Data

Jul. 7, 1998 (NZ) ..................................... 330902

(51) Int. Cl.
| | |
|---|---|
| *C12N 15/64* | (2006.01) |
| *C12N 1/00* | (2006.01) |
| *C12N 5/10* | (2006.01) |
| *C12N 15/12* | (2006.01) |
| *C12N 15/63* | (2006.01) |

(52) U.S. Cl. .................. 435/91.41; 435/243; 435/325; 435/419; 435/320.1; 536/23.5; 536/24.1

(58) Field of Classification Search ............... 536/23.5, 536/24.1; 435/325, 419, 243, 91.41, 320.1
See application file for complete search history.

(56) References Cited

OTHER PUBLICATIONS

Pang et al., *Partial Inverse PCR: A Technique for Cloning Flanking Sequences*, Bio Techniques, vol. 22, No. 6, Jun. 1997, pp. 1046-1048.

Kambadur et al., *Cloned yeast and mammalian transcription factor TFIID gene products support basal but not activated metallothionein gene transcription*, Biochemistry, vol. 87, Dec. 1990, pp. 9168-9172.

Rudnicki et al., *The MyoD Family of Transcription Factors and Skeletal Myogenesis*, BioEssays, vol. 17 No. 3, 1995, pp. 203-209.

Kambadur et al., *Mutations in Myostatin (GDF8) in Double-Muscled Belgian Blue and Piedmontese Cattle*, Genome Research, vol. 7, 1997, pp. 910-916.

(Continued)

*Primary Examiner*—Terry McKelvey
(74) *Attorney, Agent, or Firm*—Greer, Burns & Crain, Ltd.

(57) ABSTRACT

The present invention relates to a novel promoter sequence which encodes an isolated DNA molecule comprising the polynucleotide sequence of SEQ ID NO: 1 and which encodes the promoter region of the myostatin gene, or a fragment thereof, or variant thereof which has been modified by the insertion, substitution or deletion of one or more nucleotides, said fragment and variant of said polynucleotide sequence having substantially equivalent function thereto.

14 Claims, 10 Drawing Sheets

OTHER PUBLICATIONS

Lassar et al., *MyoD Is a Sequence-Specific DNA Binding Protein Requiring a Region of myc Homology to Bind to the Muscle Creatine Kinase Enhancer*, Cell, vol. 58, Sep. 8, 1989, pp. 823-831.

Gossett et al., *A New Myocyte-Specific Enhancer-Binding Factor That Recognizes a Conserved Element Associated with Multiple Muscle-Specific Genes*, Molecular and Cellular Biology, vol. 9, No. 11, Nov., 1989, pp. 5022-5033.

Wingender, Edgar, *Compilation of Transcription Regulating Proteins*, Nucleic Acids Research, vol. 16, No. 5, 1988, pp. 1879-1902.

Cohen et al., *Partal Purification of a Nuclear Protein That Binds to the CCAAT Box of the Mouse $\alpha_1$-Globin Gene*, Molecular and Cellular Biology, vol. 6, No. 3, Mar., 1986, pp. 821-832.

SEQ ID NO: 1

```
                GAATTCTTCTATGGCTATCACCATGTCCA    -10374
AAACACTACGTGAGTAAAGAAGGAGTCATTTTTTTTTAAGGGTTAAAA    -10324
AATTTAAAAATTTTTAAATTAAATTTAAAATTGAAATCTAAAAAATTTT    -10274
AAGAAAAATTTTTTTTAATCTGCAGAAACATACTCTGTATTGAGTCTATG  -10224
GTTACCAAGATCCCCCAGAACAAAACCCCAAGAATTGCAAGATTTTCT    -10174
CTTGGGAAGTGTTTGTTTACTGGAAGGCTTATTAACTCAATAATAAGGGA  -10124
GAGTAAAGACTTCAAAACTAAAGATCTGTTTTTGTCAGTTCAATCTATAT  -10074
TGTCATCTGCTCTGGAAACCCTGAGCTTGTTCTAAAGTAAACTGAACTAT  -10024
CATGAAGAAAATCAGCCATCAAAATAGTGAAAACGAACCTCTTACACTCA   -9974
GTTTTTTCTCATTTGTAAATTTAAAAAATTTAACTTCATTAAGTCTGGGG   -9924
ACCAATGTATAGCTGCAAGCAGGAATTTTATGCCTTCTTAATCCAGAGAG   -9874
GTGGGCAATGGTGTGGGTTTAGACCAGAAGTAAGGATGTGGGTGCAGCAA   -9824
ATATGACAGCCCAACTGCTGCTGCTGCTGCTAAGTCACTTCAGTCGTGTC   -9774
CGACTCTGTGTGACCCCAGAGACGGCAGCCCACCAGGCTCCCCGTCCCT    -9724
GGGATTCTCCAGGCAAGAACACTGGAGTGGGTTGCCATTTCCTTCTCCAA   -9674
TGCATGAAAGTGAAAAGTGAAAGTGAAGTCGCTCAGTCGTGTCCGACCCT   -9624
CAGTGACCCCATGGACTGCAGCCTACCAGGCTTCTCCGTCCATGGGATTT   -9574
TCCAGGCAAGAGTACTGGAGTGGGGTGCCATTGCCTTCTCCATGACAGCC   -9524
CAACTAGAGACTGCTATAACTTATATCAGAGAATCTGAAACTCCCTACAG   -9474
GCTATCTTGCTATATGTGCATTCAACATGAACAAAAGAAAATTCAAGTC    -9424
CAGTAAAAGGGCTAAAATAGTGAATCACAGACTTTTGCCAAACAACAGT    -9374
CAATGATTTGGGCAAAGGACTTAAGTAGCTATGCTTATTTGCTATTAGTA   -9324
GAATAAAGAAATGTTTGAGCCTGGTTCTCAATGCTTGAATAATAAGATTC   -9274
CTTTTCAAGGAAAAACAATTTTTTGAGAACTCATAGATAAAGTCAAAT     -9224
CTATCACTTTAGATGTCACTTGAAGCCAACTTGATTATAGTAAACAAATT   -9174
CAGCTGTAAACATTTTTTTATAACACTGTAGACACTGTATTTTTATACAC   -9124
TGTATAAATGAAGACACTGAAGATGTAAAGTGGTGACCTGGATGATCCAG   -9074
```

Fig 1

| | |
|---|---|
| AATATGCAATATGCACCAAAAACTAAGTTTTTTAAATGATACAAATGAAC | -9024 |
| TTACTTACAAAAGGGAAATAGAGTCACAGATGTAGAAAACATACAGTTAC | -8974 |
| CTAGGGGGACGGGGGGAGGGTAAACTGGGAGATAGGAATTGACACATACA | -8924 |
| CTCTACTATATATACACTAGGTAACTAATATGAACCTACTGTATAGCGCA | -8874 |
| CAGAACTCTACCCAATACTCTGTAATGACATTTATGGGAATAGAATCCAA | -8824 |
| AAAGAGCAGATATGTGTATATGTATAAACTGATTCACACCCCTTGCCTTG | -8774 |
| CCTAAACACACAGACACACACAGACACATCCATTTTGAGATTTCTTTC | -8724 |
| CTCCTCTTTGGCTACTTTTGACTCAGTTTGACCTAGATAGGACCTGTGCT | -8674 |
| GGGTAAGGGCTTTGGCAGTCTTAAGTAGTGTCAGAGCAAGCACAGTCACT | -8624 |
| CCCTAGCAAGGTCTTATTACTAGCTACAGAGTCTCTCTGTGCAGTCATAG | -8574 |
| ATCACTGAGTGCAAAAGTCCAGTGCAATGTTTGAGTCCCATGCATGCTCT | -8524 |
| CACAGAACTGAGAGAGGAGGCAAGGACACAGGACCCTCCAGTGCTGGGAC | -8474 |
| TCTCTACTGGGGTGAGCAAGAGGGAACCCAATAGAAATGCTGCGAACCAC | -8424 |
| AGAGCCACTCAGAAAGCCTGTAAATATAAACATAACAACACATTATGAAT | -8374 |
| ATATAAGTATAAGTATACCTACCAAAAAATCAGAAAGTTGAACTTTTTG | -8324 |
| TATTCAAGGGAACAGTCATTCATTTATCGGTTCAGTTATCAGTAAACACA | -8274 |
| TTTGGGAACTGTAAAAATCTAATCAGTTCAGTTCAGTTCAGTCGCTCAGT | -8224 |
| CGTGTCTCTTTGCGACTCCATGAATCGCAGCACGCCAGGCCTCCCTGTCT | -8174 |
| ATCACCAACTCCCGGCGTTCACTCAGACTTACGTCCATCGAGTCAGTGAT | -8124 |
| GCCATCCAGCCATCTCATCCTCTGTCGTCCCCTTCTCCTCCTGCCCCAA | -8074 |
| TCCCTCCCAGCATCAGAGTCTTTTCCAATGAGTCAACTCTTCTCACGAGG | -8024 |
| TGGCCAAAGTACCAAGTCTTTGAGTCTAGTCTCTTTTTTCAATGGAGAAG | -7974 |
| AAGAGGAAACCAAATTATAACTTAATTTTTATTCTTTGTATTACAAGTGT | -7924 |
| ATAATTAATACACTGGAGTTTCCATTTCAGAAAGCAAGAAGAGAAATCAC | -7874 |
| ATTTTGCAGCTTTCCTGAACTAATACAAAGAAATGCAGAAGTTTTGTTAA | -7824 |
| CTGGGATATTATTATGACACGTTGCCATAATATGAATGTCATCATCTCAA | -7774 |
| GACTGACCTGAAAACCAAAATAAAAAAAAAAGAGAGAGAGAGAGAGA | -7724 |

Fig 1 contd

```
GAGAGAAAAAAAAGAAAACCCTCCAGACCAGATTTCAGTCTACCACTTGA      -7674

GCTGACAAACATTGGCCAAATGTCCTCTACAGAACCTGTAAGTTAGTAGT      -7624

TGGTAATTATAAAACAATAAAGTATATATTTCTGCTCCTGGCAATAATTA      -7574

TGTATCAGTTAAAAAGTATACATTGTCTAAAAAATCACCATATTTGATGT      -7524

CTCATTAAAACAAAGTTACAAATATTAAGATGAGAGGACTTAAAGTTAGA      -7474

TGGGAAAATATTCAATTGAAGCAGTATAAAATGCATTACTCTGGGGCAAA      -7424

GTGTGGTCTGGAGATCCCTGGAGTGAAGACCCTTTTAGACAATCTGTGGA      -7374

GTAAGAACTGTTTTCATAACAAAGCTAAGATTTCCTTGCTATTCTCATTT      -7324

TCTCTTACGTATATAGTCGAGTTTTCCAGAAGTTCCATGTTATGTAACAT      -7274

CATCATTACTCTGTCAGCAAATAGAATACATGTTTGCATATGTCTATATT      -7224

CTAACATTTCTCATTTTTAATTTATAATTCATTAAATATTGATAGATATG      -7174

ACCCACATAAACAAAAGCTTTTCAGGATCCTGAATAACTTTTCAGAGTAA      -7124

AGGAATCTTGAGACCAAAAGGTTTGAGAATTACTGTTTTAGGGGATACAC      -7074

CTCAAGTGAAAGAGCACGCCTCATCACATTTCCACTCTATATGGAAGAAT      -7024

CTAGAAGATTGAACCTATAATTGAAGAGTGCAGGCTTTATGAAGACAGTG      -6974

ACTGTTTCTGTCTGCTTTCTCCTCAGAATTTAGCATGATGCCAGGCACAT      -6924

AATTTGTTGTTGTTCAGCTGCTAAGTCATCTCTGACTTTTTGCAACCCCA      -6874

TGAACTGCATGCAACATGCCAGGTTTCTCTGCTTTCACTATCTCCTGGAG      -6824

TTTGCTCCAACTCATGTCCATTGAGTCACTGATACCATCCAACGATCTCA      -6774

TCCTCTATAAGACACATTATAGACATTAGAATATTTTCATAAAATAATAA      -6724

GTGAATTAATACAGCTGAAACTCAAACAGCATAGGGGTTACAAGTACCAA      -6674

CTCGCGTCCAAGTTGAAAATCCACATATAATCTTAAGGTCAGCCTTGGAT      -6624

ACATGCATATCCAAGGTTCCCCATCTGAGGATTCAACCAACCTCAGATAG      -6574

TGTAGTACTGCAGTACACATTTAGTGAAAAATGTGCATATAAGTGGACCC      -6524

ATGCAGGTCAAACCTGCGTTTTCCAAGGGTCCACAGTACACACACACATG      -6474

CATACATGCATCTCTAAATGAAAGCTTTGCCATCTGACTTACTCAAGGTC      -6424

ACATAAAACGTCAGCGAGAAACCCAGAACTATATTCCAGATCTCTGTTCC      -6374
```

Fig 1 contd

| | |
|---|---|
| TATACTGTTACTCCCTGAGTCAAGGGTACTTTTGTTTTTGTTCATTTTTA | -6324 |
| TTCTGTAATCTATTGAGATCACAGATAATCAGATGTTGCCACTGTAGGAT | -6274 |
| GGCAGCCTCTCATGCTGTTATGTGAATTGAGCACTATCCAGTTTGTTTCT | -6224 |
| GGCTTTAAGTGTAATCAGAACAGTGTTATATCAAAGGGCTATCATCACAA | -6174 |
| GGAAATGGCAAGAGTGATCAGATAAATGCATCTTTCTCTCTTTTCCCAC | -6124 |
| AACAGACTCGAATTTTTCATGATTCATCCTTATTCTAATTCTTCAGTTCA | -6074 |
| GTTCAGTTCAGTCCTTCAGTCATGTCCAACTCTTTGCCACCCCATGAATC | -6024 |
| TCAGCAAGCCAGGCCTCCCTGGTCCATCACCAACTCCCAGAGTTCACCCA | -5974 |
| GACTCACGTCCATCGAGTCAGTGATGCCATCTAGCCATCTCATCCTCTGT | -5924 |
| CGTCCCCTTCTCTTCCTGCCCCCAATCCCTCCCAGCATCAGAGTCTTTTC | -5874 |
| CAATGAGTCAACTTTTCACATGAGGTGGCCAAAGTACTGGAGTTTCAGCT | -5824 |
| TTAGCATCATTCCTTCCAAAGAAATCCCAGGGCTGATCTCCTTCAGAATG | -5774 |
| GACTGGTTGGATCTCCTTGCAGTCCAAGGGACTCTCAAGAGTCTTCTCCA | -5724 |
| ACACCACAGTTCAAAAGCATCAATTCTTCGGCGCTCAGCTTTCTTCACAG | -5674 |
| TCCAACTCTCACATCCATACATGACCACAGGAAAAACCATAGCCTTGACT | -5624 |
| AGATGGACCTTTGTTGGCAAAGTAATGTCTCTGCTTTTCAATATGCTATC | -5574 |
| TAGGTTGGTCATAACTTTCCTTCCAAGGAGTAAGCATCTTTTAATTTCAT | -5524 |
| GGCTGCAGTCACCATTTGTAGTGATTTTGGAGCCCAGAAAAATAAAGTCT | -5474 |
| TGACACTGTTTCCACTGTTTCCCCATCTTATTTCCCATGCAGTGATGGGA | -5424 |
| CCGGATGCCATGATCTTAGTTTTCTGAATGTTGAGCTTTAAGCCAACTTT | -5374 |
| TTCAATCTCCTCTTTCACTTTCATCAAGAGGCTTTTGAGTTCCTCTTCAC | -5324 |
| TTTCTGCCATAAGGGTGGTGTCATCTGCATATCTGAGGTTATTAATATTT | -5274 |
| CTCCCGGCAATCTTGATTCCAGCTTGTGCTTCTTCCAGCCCAGTGTTTCT | -5224 |
| CATGATGTACTCTGCATAGAAGTTAAATAAGCAGGGTGACAATATACAGT | -5174 |
| CTTGACATCCTCCTTTTCCTATTTGGAACCAGTCTGTTGTTCCATGTCCA | -5124 |
| GTTCTAACTGTTGCTTCCTGACCTGCATACAGGTTTCTCAAGAGGCAGGT | -5074 |
| CAGGTGGCAGGTCAGGTGGTCAGGAACATCTCTTTCAGAATTTTTGACAG | -5024 |

Fig 1 contd

```
TTTATTGTGATCCACACAGTCAAAGGCTTTGGCATAGTCAATAAAGCAGA          -4974
AATAGATGTTTTCTGGAACTCTCTTGCTTTTCGATGATCCAGCAGATG            -4924
TTGGCAATTTGATCTCTGGTTCCTCTGCCTTTTCTAAAACCAGCTTGAAC          -4874
ATCAGGAAGTTCATGGTTCACGTATTGCTGAAGCCTGGCTTGGAGAATTT          -4824
AGAGCATTACTTTACTAGCATTACTTTTCACAATAAACTGTGGAAAATTC          -4774
TGAAAGAGATGGGCATACCAGACCACCGGATCTGCCTCTTGAGAAATTTG          -4724
CATGCAGGTCAGGAAGCAACAATTAGAAGTGGACATGGAACAACAGACTG          -4674
GTTCCAAATAGGAAAAGGTGTTCGTCAAGGCTGTATATTGTCACCCTGTT          -4624
TATTTAACTTCTATGCAGAGTACATCATGAGAAACGCTGGGCTGGAAGAA          -4574
GCACAAGCTGGAATCAAGATTTCCGGGAGAAATATCAATAACCTCAGATA          -4524
TGCAGATGACACCACCCTTATGGCAGAAAGTGCAGAGGAACTAAAAAGCC          -4474
CCTTGATGAAAGTGAAAGTGGAGAGTGAAAAGTTGGCTTAAATCTCAAC           -4424
ATTCAGAAAACGAAGATCATGGCATCCGGTCCCATCACTTCATGGGAAAT          -4374
AGATGGGGAAACAGTGGAAACAGTGTCAGACTTTATTTTTCTGGGCTCCA          -4324
AAATCACTACAAATGGTGACTGCAGCCATGAAATTAAAAGATGCTTACTC          -4274
CTTGGAAGGAAAGTTATGACCAACCTAGATAGCATATTGAAAAGCAGAGA          -4224
CATTACTTTGCTAACAAAGGTCCATCTAGTCAAGGCTATGGTTTTCCTG           -4174
TGGTCATGTATGGATGTGAGAGTTGGACTGTGAAGAAAGCTGAGTGCCGA          -4124
AGAATTGATGCTTTTGAACTGTGGTGTTGGAGAAGACTCTTGAGAGTCCC          -4074
TTGGACTGCAAGGAGATCCAACCAGTCCATTCTGAAGGAGATCAGCCCTG          -4024
GGATTTCTTTGGAAGGAATGATGCTAAAGCTGAAACTCCAGTACTTTGGC          -3974
CACCTCATGTGAAGAGCTGACTCATTGGAAAAGACTCTGATGCTGGGAGG          -3924
GATTGGGGGCAGGAGGAGAAGGGGGCGACAGAGGATGAGATGGCTGGATG          -3874
GCATCACTGACTCAATGGACGTGAGTCTGTGTGAACTCTGGGAGTTGGTG          -3824
ATGGACAGGGAGGCCTGGCGTGCTTTGATTCATGGGGTCACAAAGAGTCG          -3774
GACACGACTGAGCGACTGATCTGTCTCTCTCTTACTAGCATGTGTCTCCT          -3724
CCTTTTTTTGCCACATCATCAAACTCCTGGCAAACTTCACATTAATAACA          -3674
```

Fig 1 contd

| | |
|---|---|
| TTTGGGAGCTTCCAGAATGCAAACAGTGAAACCATTAATGTTTTTTGGGA | -3624 |
| AATATGCTTTATACTCTCAATGTTGTTTTGAAACGCACACCCCCTCCCCT | -3574 |
| GCCGCCTGGTGTTTGTAAGACAGTTGAGAGAAGTTTGCTTGCTACCTTAC | -3524 |
| TTATGGTTACACAAACGTAAGGCCCCCTGAGTACAAAGAAGAACAGGGGG | -3474 |
| AACGCAAACTTCAGGCCCTGTGAGGAGGGGCACTGGACTCCTGTGAGAAG | -3424 |
| AAACTGCTTTCAAAGAATTCCTGGGAGAAATTCTCTATGCACTCATCCTA | -3374 |
| GCAACAAAGTCCTGTCCGAAGTTAGGCCCGCAGCACCCACACGGCAGTGA | -3324 |
| AGGTTCCTACTGCTGGTGAACCTTGCTGCTCCGAAGCCATAGGAAGGTTG | -3274 |
| CAAATCCCGGCACTGGAGAAGGAAAACACGTTCTTGAAATTTCTTGAGTA | -3224 |
| CCTCTTAATTCATTCAATGCTGACCTCCGGAGATTGGATAGAGCTGACTC | -3174 |
| TCATTATTCACAGTGGTTATGTTCTACCCAATCACTGCCAACATGAATAA | -3124 |
| GTGATTCCTGAACCACTGCCCCTAGGGGAACTACAAGGTTAGATTCCCGT | -3074 |
| CAGCCTCTGGTCACGTTTTGTTAACCAATCAATAAATAACCTTGTTTTG | -3024 |
| TGTGCATTTCTGTTTTAAAATATCTTTATTTAATACGTACTGCTAATTCT | -2974 |
| TCAACATTTGGTTCACAACCAAAAGGCCCTATTAACTGGAAGCCCTGAAT | -2924 |
| GAAGCTTACATAACACACATTGTTTTTCTATGAGGAAAAATTTTTCCTTC | -2874 |
| AGTCCTGCCACAGCCTTCTTGCTTAAAATTGTGGACAAAATATACATAAC | -2824 |
| ATGAAACTGACTATTATTTAACTGATTTTAACTGTACAGTTCAGTGGCAT | -2774 |
| TAAGTACACTTACCTTGCTGTGGAACTATGATCAACATTCATCTCTAGAA | -2724 |
| CTTTTTGATCTTCTCGAATTGAAAACTCTGCATCTATTGCACAGTAGCTT | -2674 |
| TCCCCATCACACCGCACCCTTCCTCCAGCCCCCGGCACCACCATCCTT | -2624 |
| CTTTCCATGACAGTCATCCTGTGCCTAGGAACACAGCCCTTCAACACTAC | -2574 |
| GCTTGGGGGCACTGTAAGCAACAGGATCACTCCCTACCGCCACCAAATG | -2524 |
| CACACAAAATATAAAAAGCATGGTGGCATATCGATTGCAAAAAGGGTGC | -2474 |
| TTGCTAAGTATGAGGGCTGAAACAAGGCAGAGAATTGACTAGGTTGACCT | -2424 |
| CAGCTGGGATCCTGTGTGTTGGAAGCCTCAAATTTTCCATTGTTCTGTGC | -2374 |
| ATACGCACAAATGCTTATAAAAGCACTGTAAGGATTGATTATGAAGTTAA | -2324 |

Fig 1 contd

| | |
|---|---|
| GATAAATCTCAGCAAGACATAAATGTGCAAGCACGGGATCCATGAATAAC | -2274 |
| GAGCACTGACCATGTGGAAATGATAATCTTTGTTTCCTTTATTCCAGGCA | -2224 |
| GTAAGGAGAAAGCGCTCACAGGGCTGCCTTACACCATTTTACTAGAGAGC | -2174 |
| TAGCCTATGTCAGTCGGTAGCTGGCAATTACAAACTGAAGCAGTTCTAGT | -2124 |
| TCATGTGGAGGATGAATTTAACCATAATCTCAACCCCCTCTGCATGAAAC | -2074 |
| AGAGACTAAGTACTCAAGTACCAGTTATCAGTCACTTACTATATGACAGG | -2024 |
| CACTGTACTCAACAATTTACATGTATTATTGAATTACATGCCCCCAACAC | -1974 |
| TCTATGAGGAAGCTGAAGGTTAGAGAAGTATCTCATTCATTATTACACAG | -1924 |
| TGGCAAACTGAGATCTGAACTCAGGTCTATCCAACTCCAGGACCTGAGAT | -1874 |
| CCCAATTGCTACACAATTCTAATCAAGTTAAAAGGGAAAAAGGATTTGAT | -1824 |
| TTGCTCAGAAGTGTATAGGGGCATATGTTACAATTATAACATTACAAAGA | -1774 |
| TTTATATGTTGAAAAATAAATTTATCAAACAAATAAAACTTTATAAGCCT | -1724 |
| GATCTAATACTGCTCCGCAACAAAGACTATCTGAAATCCTTCAGGGCATC | -1674 |
| TGGTTTGTGTCTGGTTTTCCTTAATCTTTAATGATGGGCAAATCTAATGC | -1624 |
| ATTATGTAAGGCCATTTTTTCTCAAGAGATGTAGATACCTCTTAAGAATT | -1574 |
| TGATGAAAATGCATTAACTTTTCAGGCTACTGAGTTGCATTTTAGTGCAC | -1524 |
| TGAGGCAGTAAATTAGTGTACAATGTGCGAAAGTAGTGACCTAAAAAATA | -1474 |
| AATATTTGATATGAACCACTGCACTCTCTTGGGGAAAAAGTAATGGATT | -1424 |
| AACTCTCTTAGGAGTCCTTAGCTTCCCCAAAAGTAGTAGGAAAAATAAAT | -1374 |
| CTCCTGTGGCCTGGAAACAGCTTCTGTTTCTTGCTGGCTATATTTGTTTA | -1324 |
| GGTTTTTAATAGTTCATTTGATTAGACCTTGTGGCTCCCAAAGCTAAGGT | -1274 |
| E-box (4) | |
| TGAGAGTTTGATCCCTACAGAGGCCACTTCAATTTAGAGAACAAAAGCC | -1224 |
| CCATTCTCTGCTCCCAGACCTTACCCCAAATCCCTGCCAGGTGTCTGCCC | -1174 |
| TCCGGTCAAATGAGAAACTGGCAAAGGAAGTACTAGGAGGTCGCACAGTA | -1124 |
| E-box (3) | |
| CTAGGAAGTAGAAAAATGGACTAGCACACTACTGAGAAGCAGAAAAATGG | -1074 |

Fig 1 contd

```
GCACCCTTCATGATGGTGTTCCTTTCCCTTTCTGTGTTCACAATGCTCCG      -1024
ATATAATTTACAGAGGGTAGATAACTACATTTTTTCTTTTACCACTGGA       -974
AGGCTGAGGAAAACTTTGTTACCCATCATAAAATTCACTATCTTCTAAGT      -924
CATTCTATGTTATTCTAAGATCAAATAGCTGACAATATCCTCTTTGTAAT      -874
AAACAATGAAAAACACATCCTCTGAGCAATATTAATCTGCAACTTTAGG       -824
ATAGGAAGTAACTTAATACTAGTCAATTGAAACTGAAATACAATTTTCAT      -774
ATGAATAAAGATATTATTTAAAAGTAATTCCATGAGCAATTTAATATTA       -724
AAGTAGGATTTTCATTATGTGTTAAGAATTTATTCAGGGAAACAAGTTTC      -674
TCAAATTATAGCAGAAAATCTTTTACTAGTATCACAGTCTTTTCATTTAA      -624
GTCTTCCTGAATAAATCTGTATTTTCTAATTATACAAGACTAAAAATAAT   -574
                                        MEF2-site
TTAATATAACAAATAAAATTATTTTTACTTCAAATGCTTACTTAAATAGT   -524
                                  E-box (2)
ATAAAATCATTTTATTTTCTGAGGGAAAAGCATATCAACTTTTTAAGTAT   -474
TATA-box (3)
GAAGTGTAAATTAAGATTTATTCACTTAAATTATAATTTTTAAAGTTTCA      -424
CATATAAAGATGAATAAGATCTAAGTGTATATGTTATTGTTAATAAAGTT      -374
TTTAATTTTTCGCATGTCACATACAGCCTTTATTATTCATAGATTTATTC      -324
CTTTTAAGAAGTAGTCAAATGAATCAGCTCACCCTTGACTGTAACAAAAT    -274
                E-box (1)
ACTGTTTGGTGACTTGTGACAGACAGGGTTTTAACCTCTGACAGCGAGAT      -224
TCATTGTGGAGCAAGAGCCAATCACAGATCCCGACGACACTTGTCTCATC    -174
                  CAAT-box
AAGTTGGAATATAAAAGCCACTTGGAATACAGTATAAAAGATTCACTG    -124
         TATA-box (2)           TATA-box (1)
GTGTGGCAAGTTGTCTCTCAGACTGGGCAGGCATTAACGTTTGGCTTGGC      -74
GTTACTCAAAAGCAAAAGAAAAGTAAAAGGAAGAAGTAAGAACAAGGGAA      -24
```

Fig 1 contd

AAGATTGTATTGATTTTAAAACC<u>ATGCAAAAACTGCAAATCTCTGTTTAT</u>    +27

<u>ATTTACCTATTTATGCTGATTGTTGCTGGCCCAGTGGATCTGAATGAGAA</u>    +77

<u>CAGCGAGCAGAAG</u>    +90

FIG. 1. Nucleotide sequence of the 10,492-basepair promoter-enhancer region of bovine myostatin. Total length of the DNA sequence is 10,492 basepairs (bps) which consist of 10,402 bps of upstream and 90 bps of coding sequence. The coding sequence of myostatin is underlined. Nucleotides and the relative position of putative nucleotide motifs are numbered with respect to the translation start site (+1 bp).
Consensus sequences for basic functional elements of a mammalian promoter (TATA and CAAT boxes) and for known muscle specific transcription factors (E-box and MEF2 sites) are bolded in the sequence and they are listed below.

| | |
|---|---|
| TATA-boxes[1]: | -139 bps(1); -163 bps(2); |
| | -524 bps(3) |
| CAAT-box[2]: | -206 bps |
| E-boxes[3]: | -308 bps(1); -543 bps(2) |
| | -1167 bps(3); -1309 bps(4) |
| MEF2 site[4]: | -584 bps |

Fig 1 contd

ISOLATED DNA MOLECULE COMPRISING THE PROMOTER SEQUENCE OF A BOVINE MYOSTATIN GENE

The present invention concerns the novel promoter sequences of the myostatin gene, DNA constructs comprising the novel promoter sequences operably linked to the coding sequence of a gene of interest, to vectors containing the promoter or construct and host cells containing such vectors.

BACKGROUND OF THE INVENTION

A promoter region of a gene is one which controls the expression of the gene. The myostatin gene was isolated and sequenced and the sequence published (McPherron A C; Lawler A M and Lee S J; Nature 387, 1 May 1997; WO94/21681). However the sequence of the promoter region of this gene has not been isolated, sequenced or published to date.

Myostatin, also known as growth and differentiating factor-8 (GDF-8), is structurally related to the transforming growth factor β (TGF-β) superfamily (McPherron et al 1997). The myostatin gene has been shown to inhibit muscle growth and initial research concluded that targeted disruption of the myostatin gene in mice leads to a twofold increase in muscle mass (McPherron et al 1997) indicating that the myostatin gene is a negative regulator of muscle mass.

Three of the present inventors (Kambadur, Sharma and Bass) have identified a mutation of the myostatin gene in "double muscled" Belgian Blue cattle comprising an 11 bp deletion (Kambadur et al 1997). This mutation negates the effect of myostatin and leads to a 30% or 40% increase in muscle mass.

The inventors have further observed two Belgian Blue sire lines which possess the same Belgian blue allele, i.e. the 11 bp deletion, but which is being expressed in very small amounts. On a northern blot, two bands were seen suggesting that in these animals there is a double mutation of the myostatin gene, ie hypomorphic alleles. This strongly suggests that a failure in the upstream regions of the myostatin gene have resulted in a lack of expression of myostatin and as a consequence increased muscle growth.

SUMMARY OF THE INVENTION

The present invention provides an isolated DNA molecule having a polynucleotide sequence of SEQ ID NO. 1 of FIG. 1 and which encodes the promoter region of the bovine myostatin gene, or a fragment or variant of said polynucleotide sequence which has been modified by the insertion, substitution or deletion of one or more nucleotides having substantially equivalent function thereto.

In a further aspect, the present invention provides an isolated DNA construct comprising the DNA molecule of the invention operably linked to a heterologous gene of interest such that the heterologous gene is under transcriptional control of the DNA molecule of the invention.

The DNA molecule may have been isolated from a natural source or may comprise cDNA.

In a further aspect the invention provides recombinant expression vectors which contain a DNA molecule of the invention as defined above, and/or the DNA construct of the invention, and hosts transformed with such vectors and capable of induction of the DNA molecule and/or of inducible expression of the heterologous gene of the DNA construct. In a further aspect the invention provides a method of producing the sequence encoded by the DNA molecule comprising culturing a host cell, transfecting said host cell with a vector containing the DNA molecule of the invention or a fragment or variant thereof and cloning the DNA sequence by known methods.

In still a further aspect, the invention may be said to consist in a method of diagnosing muscle cell disorders in an animal, including a human, using the myostatin gene promoter sequence as defined above, as a diagnostic probe. The diagnostic method may comprise the steps:
i) obtaining a tissue or blood sample from an animal or human;
ii) isolating the DNA by known methods;
iii) optionally isolating myostatin DNA;
iv) probing said DNA with a probe complementary to the myostatin gene promoter sequence;
v) optionally amplifying the amount of myostatin promoter DNA using PCR technology;
vi) analysing the myostatin promoter sequence DNA obtained with the probe for any mutations which may result in muscle cell disorders; and
vii) diagnosing muscle cell disorders caused by myostatin gene promoter sequence anomalies.

The probe may comprise a complementary sequence to a part or the whole of the nucleotide sequences of myostatin promoter DNA of SEQ ID NO. 1.

The probe is preferable genomic or cDNA.

In still a further aspect, the invention consists in a method of selection of animal breeds that express low levels of myostatin. This method comprises the steps:
i) obtaining a tissue or blood sample from an animal or human;
ii) isolating the RNA by known methods;
iii) determining the transcript level (mRNA) of myostatin gene, using Northern blot or RT-PCR technology or RNase Protection Assay.

Preferably the animal is a cow, bull, sheep, pig, human or any other mammal, poultry, fish or any other economically important livestock breed.

In still a further aspect, the invention consists in a method of expressing a heterologous gene of interest specifically in muscle cells comprising the steps:
i) isolating the coding sequence of said heterologous gene;
ii) ligating said coding sequence of said heterologous gene to the myostatin promoter sequence so that said coding sequence is under the transcriptional control of said myostatin promoter;
iii) inserting the ligated construct into a suitable expression vector;
iv) introducing the expression vector into a muscle host cell; and
v) optionally measuring the expression of the heterologous gene by recovering the product.

The method may be carried out in vitro in muscle cells in culture or in vivo in an animal including a human.

In a still further aspect, the present invention provides a method of producing a heterologous polypeptide or peptide comprising the steps of:
(a) culturing a host cell which has been transformed or transfected with a vector containing the DNA construct as defined above to express the heterologous polypeptide or peptide encoded by the heterologous gene; and optionally
(b) recovering the expressed polypeptide or peptide.

In a still further aspect, the present invention provides a non-human transgenic mammal that expresses a heterologous polypeptide or peptide in their muscle cells, said non-human mammals having been transfected with the DNA constructs of the present invention.

The heterologous gene of interest may be selected from the group consisting of:
a) Myogenic regulatory factors;
b) Myostatin and Myostatin receptor;
c) Oncogenes;
d) Genes that regulate muscle growth or differentiation;
e) Muscular dystrophy gene; and
f) Any genes expressed in muscle.

The expression vector may be selected from the group consisting of Eukaryotic vectors, retroviral vectors or any vectors that are used for gene therapy.

The muscle host cell may be selected from in vitro cell culture lines selected from the group consisting of any primary culture of myoblasts or transformed myoblasts, satellite cells or any cell culture where myostatin promoter is active. Alternatively the host muscle cell may comprise a skeletal muscle cell in vivo in a host animal.

The host animal may be selected from the group comprising cow, bull, sheep, pig, horse, rat, mouse, poultry, fish or human.

In a still further embodiment the present invention provides a method of expressing myostatin or antisense to myostatin or ribozymes or any foreign gene in a host muscle cell/myoblast comprising the steps: preparing a construct comprising the myostatin promoter ligated to a coding sequence of interest, so that said coding sequence is under transcriptional control of the myostatin promoter, cloning said construct into gene therapy vectors by standard cloning procedure and transfecting them into a desired cell line or tissue of a live animal or human.

Preferably the host muscle cell is selected from the group consisting of a skeletal muscle cell, a somite, a myoblast or any mesodermally derived cells.

In a still further aspect the present invention provides a method of expressing dominant negative forms of myostatin or of any gene of interest in a host muscle cell comprising the steps: cloning the myostatin promoter ligated to desired mutated or wild type gene wherein said gene is under the transcriptional control of said myostatin promoter, into gene therapy vectors by standard cloning procedures and transfecting them into a desired cell line or tissue of a live animal or human.

Preferably the host muscle cell is selected from a skeletal muscle cell, a somite, a myoblast or myotube.

The method may be carried out in vitro in the host muscle cell in culture or in vivo in a host animal. The host animal may be selected from the group consisting of cow, bull, sheep, pig, horse, rat, mouse, human, poultry or fish.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples.

DESCRIPTION OF FIGURES

One preferred form of the present invention will now be described with reference to the accompanying drawing in which:

FIG. 1 shows the promoter sequence of the myostatin gene isolated from bovine muscle (SEQ ID NO. 1)—indicating consensus sequences for basic functional elements of known transcription factor binding sites.

Definitions

Figure 2:
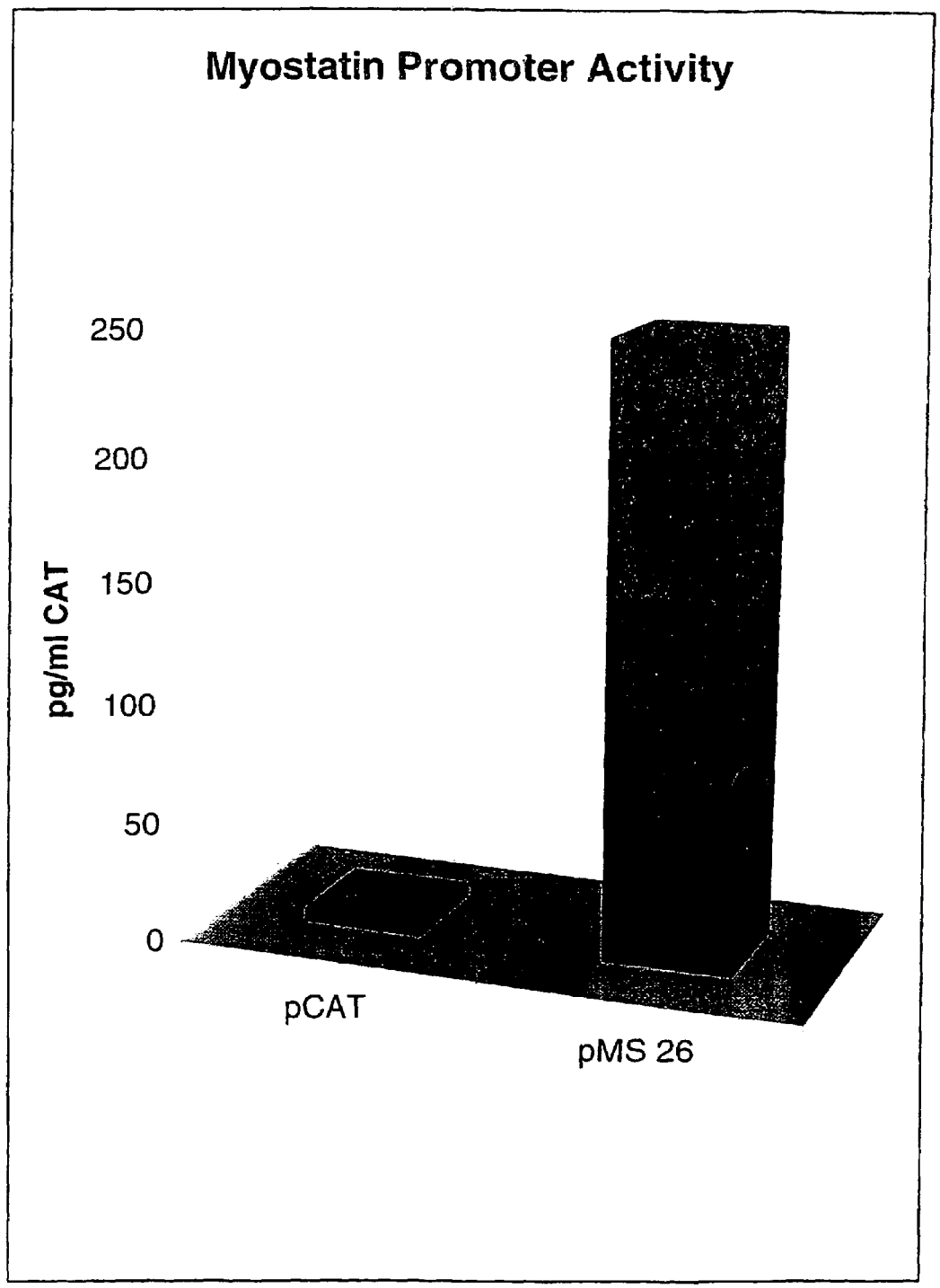
FIG. 2 shows the promoter activity of the promoter sequence of FIG. 1.

The term "isolated" means substantially separated or purified away from contaminating sequences in the cell or organism in which the nucleic acid naturally occurs and includes nucleic acids purified by standard purification techniques as well as nucleic acids prepared by recombinant technology and those chemically synthesised.

The term "variant" as used herein refers to a DNA molecule wherein the nucleotide sequence is substantially identical to the nucleotide sequence set out in FIG. 1. The variant may be arrived at by modification of the nucleotide sequence of the DNA molecule by such modifications as insertion, substitution or deletion of one or more nucleic acids, such modifications comprising neutral mutations which do not affect the functioning of the DNA molecule.

The term "substantial sequence identity" means that two nucleotide sequences, when optimally aligned, such as by the programs Clustal W using default gap weights, share at least 60 percent sequence identity, preferably at least 80 percent sequence identity, more preferably at least 90 percent sequence identity and most preferably at least 95 percent sequence identity or more.

The term "DNA construct" means a construct incorporating the nucleic acid molecule of the present invention, or a fractional fragment, neutral mutation or homolog thereof in a postion whereby a heterologous coding sequence is under the control of and operably linked to the promoter sequence of the invention and is capable of expression in a host cell.

The term "neutral mutation" means a mutation, ie a change in the nucleotide or polypeptide sequence such as by deletion, substitution, inversion or insertion, which have no effect on the function of the encoded promoter sequence.

A fragment of a nucleic acid molecule according to the present invention is a portion of the nucleic acid that is less than full length and comprises at least a minimum length capable of hybridising specifically with a nucleic acid molecule according to the present invention (or a sequence complementary thereto) under stringent conditions as defined below. A fragment according to the present invention has at least one of the biological activities of the nucleic acid or polypeptide of the present invention.

Nucleic acid probes and primers can be prepared based on nucleic acids according to the present invention eg the sequence of SEQ ID NO: 1 or 2. A "probe" comprises an isolated nucleic acid attached to a detectable label or reporter molecule well known in the art. Typical labels include radioactive isotopes, ligands, chemiluminescent agents, and enzymes.

"Primers" are short nucleic acids, preferably DNA oligonucleotides 15 nucleotides or more in length, which are annealed to a complementary target DNA strand by nucleic acid hybridization to form a hybrid between the primer and the target DNA strand, then extended along the target DNA strand by a polymerase, preferably a DNA polymerase. Primer pairs can be used for amplification of a nucleic acid sequence, eg by the polymerase chain reaction (PCR) or other nucleic acid amplification methods well known in the art. PCR-primer pairs can be derived from the sequence of a nucleic acid according to the present invention, for example, by using computer programs intended for that purpose such as Primer (Version 0.5© 1991, Whitehead Institute for Biomedical Research, Cambridge, Mass.).

Methods for preparing and using probes and primers are described, for example, in Sambrook et al. Molecular Cloning: A Laboratory Manual, 2nd ed, vol. 1–3, ed Sambrook et al. Cold Spring Harbour Laboratory Press, Cold Spring Harbour, N.Y., 1989.

Probes or primers can be free in solution or covalently or noncovalently attached to a solid support by standard means.

The term "operably linked" means a first nucleic acid sequence linked to a second nucleic acid sequence when the first nucleic acid sequence is placed in a functional relationship with the second nucleic acid sequence. For instance, a promoter sequence of the present invention is operably linked to a coding sequence of a heterologous gene if the promoter affects the transcription or expression of the coding sequence.

A "recombinant" nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, eg, by genetic engineering techniques.

Techniques for nucleic acid manipulation are described generally in, for example, Sambrook et al. (1989).

The term "stringent conditions" is functionally defined with regard to the hybridization of a nucleic acid probe to a target nucleic acid (ie to a particular nucleic acid sequence of interest) by the hybridization procedure discussed in Sambrook et al. (1989) at 9.52–9.55 and 9.56–9.58.

Regarding the amplification of a target nucleic acid sequence (eg by PCR) using a particular amplification primer pair, stringent conditions are conditions that permit the primer pair to hybridize only to the target nucleic acid sequence to which a primer having the corresponding wild type sequence (or its complement) would bind.

Nucleic acid hybridization is affected by such conditions as salt concentration, temperature, or organic solvents, in addition to the base composition, length of the complementary strands, and the number of nucleotide base mismatches between the hybridizing nucleic acids, as will be readily appreciated by those skilled in the art.

DETAILED DESCRIPTION OF THE INVENTION

As defined above, in its primary aspect, the present invention is directed to a novel promoter sequence of the myostatin gene and the uses thereof as a diagnostic test for muscle cell disorders and genetic marker for the selection, in particular, of cattle/sheep breeds that express low levels of myostatin. The novel promoter sequence is also useful for expressing foreign genes or dominant negative forms of myostatin in muscle.

The novel promoter sequence of the present invention comprises an isolated DNA molecule having a polynucleotide sequence of SEQ ID NO: 1 of FIG. 1 or a fragment or variant thereof having substantially equivalent transcriptional activity there.

The technology used to isolate the myostatin promoter from a genomic DNA library is described generally in Sambrook et al, "Molecular cloning", Second Edition, Cold Spring Harbour Press (1987).

An initial step involves the use of a specific myostatin DNA probe followed by cloning in a host cell and subsequent amplification using PCR technology.

Preferably, the host cell in which the DNA sequence encoding the myostatin promoter is cloned is a prokaryote such as *E. coli*. Other prokaryotes can also be used, for example bacilli such as *Bacillus subtilis* and enterobacteriaceae such as *Salmonella typhimurium* or *Serratia* marcesans.

In general, where the host cell is a prokaryote, cloning vectors containing replication and control sequences which are derived from species compatible with the host cell are used. The vector may also carry marking sequences which are capable of providing phenotypic selection in transformed cells. For example, *E. coli* has commonly been transformed using pBR322, a plasmid derived from an *E. coli* species which contains genes for ampicillin and tetracycline resistance and thus provides easy means for identifying transformed cells.

In addition to prokaryotes, eukaryotic microbes, such as yeast may also be used, for example, *Saccharomyces cerevisiae* or cultured cells derived from multicellular organisms such as mammals and insects may be used as hosts. Examples of mammalian cultured cells which may be useful are HeLa cells and Chinese Hamster Ovary (CHO) cells, myoblasts, muscle cells, fibroblasts, and satellite cells.

Suitable cloning vectors for use in mammalian cells include SV40 or other suitable viral vectors.

The DNA molecule of the invention can be contained within a DNA molecule isolated from an appropriate natural source (muscle, blood) or can be produced as intron-free cDNA using conventional techniques. cDNA is preferred.

The invention also contemplates variants of the DNA molecule which differ from the native sequence by the insertion, substitution or deletion of one or more nucleotides. These variants can be made through selective synthesis of the DNA using an appropriate synthesizer or by modification of native DNA by, for example, site specific or cassette mutagenesis or by any other techniques known in the art. Such variants may be between 60–95% homologous in the DNA sequence of SEQ ID NO: 1 of FIG. 1 and have substantially equivalent function thereto.

The production of DNA fragments, probes and primers is also well within the capabilities of the skilled worker.

The DNA molecule may comprise a native bovine myostatin isolated from any appropriate natural source or can be produced in the form of a synthetic oligonucleotide where the size of the active fragment to be produced permits. By way of example, the Triester method of Matteucci et al, J. Am. Chem. Soc. Vol 103: 3185–3191 (1981) may be employed.

Once obtained, the DNA molecule is treated to be suitable for insertion together with the selected control sequence into the appropriate cloning vector. To this end the DNA is cleaved, tailored and religated as required.

Cleavage is performed by treating with restriction enzyme(s) in a suitable buffer. Any of the large number of commercially available restriction enzymes can be used as specified by the manufacturer. After cleavage, the nucleic acid is recovered by, for example, precipitation with ethanol.

Tailoring of the cleaved DNA is performed using conventional techniques. For example, if blunt ends are required, the DNA may be treated with DNA polymerase I (Klenow), phenol and chloroform extracted and precipitated by ethanol.

Re-ligation can be performed by providing approximately equimolar amounts of the desired components, appropriately tailored for correct matching and treatment with appropriate ligase (eg T4 DNA ligase).

In a further aspect, the present invention consists in a DNA construct comprising the DNA molecule of the invention, ie the bovine myostatin promoter, operably linked to a heterologous gene of interest such that the heterologous gene is under the transcriptional control of the bovine myostatin promoter.

The constructs may comprise a bovine myostatin promoter operably linked to a heterologous gene of interest selected from the group comprising myogenic regulatory factors; myostatin and myostatin receptor; oncogenes; genes that regulate muscle growth and differentiation; the muscular dystrophy gene; and any other genes expressed in muscle.

Similar techniques to those described above would be employed when making constructs comprising the myostatin promoter ligated to a foreign ie, heterologous gene which may be desired to be expressed in muscle cells either in vitro or in vivo.

In vitro expression may occur in cultured muscle cells such as fibroblasts, HeLa cells or in cultured myoblasts or myotube cells using replicable transfer vectors suitable for use in the expression of the DNA constructs of the invention to produce a heterologous protein.

The replicable transfer vector may be selected according to the host or host cell to be used. Useful vectors will generally have the following characteristics:
(a) the ability to self-replicate;
(b) the possession of a single target or any particular restriction endonuclease cleavage site; and
(c) desirably, carry genes for a readily selectable marker such as antibiotic resistance.

Two major types of vectors possessing these characteristics are plasmids and bacterial viruses (bacterophages or phages).

Suitable eukaryotic expression vectors which may be employed include, for example pcDNA 1.1, and the expression product could be isolated and measured.

In vivo expression of a construct of the invention could be brought about by known gene therapy techniques. For example the myostatin promoter could be inserted in the Moloney murine leukemia virus (MoMuLv), Harvey murine sarcoma virus (HaMuSv), murine mammary tumor virus (MuMTV), and Rous Sarcoma Virus (RSV). A number of additional retroviral vectors can incorporate multiple genes. By inserting the myostatin promoter into viral vectors, the vector could now be used for expressing muscle specific genes.

In the construction of a vector it is an advantage to be able to distinguish the vector incorporating the foreign DNA from unmodified vectors by a convenient and rapid assay. Reporter systems useful in such assays include reporter genes, and other detectable labels which produce measurable colour changes, antibiotic resistance and the like. In one preferred vector, the β-galactosidase reporter gene is used, which gene is detectable by clones exhibiting a blue phenotype on X-gal plates. This facilitates selection. In one embodiment, the β-galactosidase gene may be replaced by a polyhedron-encoding gene; which gene is detectable by clones exhibiting a white phenotype when stained with X-gal. This blue-white colour selection can serve as a useful marker for detecting recombinant vectors.

Once selected, the vectors may be isolated from the culture using routine procedures such as freeze-thaw extraction followed by purification.

In a still further aspect, the invention provides a method of selecting animals which have low myostatin expression which includes essentially the use of the myostatin promoter sequence as a genetic marker. This could be accomplished by PCR amplification of the myostatin promoter using genomic DNA isolated from blood with the primers designed along the promoter sequence and scanning the genomic DNA for mutations.

Non-limiting examples illustrating the invention will now be provided.

It will be appreciated that the above description is provided by way of example only and variations in both the materials and techniques used which are known to those persons skilled in the art are contemplated.

EXAMPLE 1

1. Cloning of Myostatin Gene Promoter

5' upstream regulatory sequences of bovine myostatin gene was isolated from a bovine lambda genomic library (Stratagene) by the method of Sambrook et al (1989). The library was screened with a 500 bp genomic DNA (−1700 to −1200) isolated by inverse PCR. The entire genomic clone was subcloned into pBluescript and sequenced.

This PI-PCR procedure is a modification of the method described by K M Pang and D A Knecht (1997). A series of Sau3A1 digests were prepared for use as templates for PCR. Sau3A1 (New England Biolabs, USA) digests of 10 $\mu$g aliquots of bovine genomic DNA were carried out at 2, 0.5, 0.125, 0.031, 0.008, 0.004, 0.002 U/$\mu$g DNA for 1 hour at 37° C. The reactions were stopped by heating at 65° C. for 20 min. Two micrograms of each reaction mixture were separated on a 1% agarose gel to check the extent of cutting. On the basis of extent of digestion, one partial digest (0.008 U of Sau3A1/$\mu$g DNA) was chosen for further work. The DNA was then ethanol precipitated and resuspended in 1× ligase buffer to the final concentration of 5 ng/$\mu$l. T4 DNA ligase (New England Biolabs, USA) was added to a concentration of 4 U/$\mu$l to carry out ligation at 22° C. overnight. Ligation was then stopped by heating at 65° C. for 20 min, phenol and then chloroform-extracted, ethanol precipitated and resuspended in sterile water to a concentration of 50 ng/$\mu$l. Two primers (5'-CTGCTCGCTGTTCTCATTCA-GATC (SEQ ID NO: 2) and 5'-ATCCTCAGTAAACT-TCGCCTGGA (SEQ ID NO: 3)) facing outwards from 5' translated DNA sequence of bovine myostatin were used to carry out PI-PCR. PCR was carried out in 50 $\mu$l reaction volume containing 250 ng re-ligated DNA, 0.2 mM each dNTP (Gibco BRL, USA). 0.8 $\mu$M of each primer and 2 $\mu$l of Elongase enzyme mix (Gibco BRL, USA) in 1×"B" buffer supplied by the manufacturer was added. PCR was performed for 35 cycles at: 94° C. for 30 sec, 55° C. for 2 min, 68° C. for 6 min. PCR product was separated on a 1% agarose gel and a 2-kb band was excised, purified with the Wizard PCR Preps DNA Purification System (Promega, USA) and cloned by the TA Cloning System (Invitrogen, USA). 2-kb insert was then sequenced using M13 forward, reverse, 5'-GGCTGTATGTGACATGCG (SEQ ID NO: 4) and 5'-TGAACCACTGCACTCTCTTG (SEQ ID NO: 5) primers.

2. Construction of CAT Reporter Vector:

3.3 kb of myostatin upstream genomic DNA was PCR amplified using bovine genomic DNA as template. The primers used in the PCR are as follows GGGGTAC-CCCAATTCCTGGGACAAATTCTCTA (SEQ ID NO: 6) (FORWARD) GGGGTACCGGTTTTAAAATCAATA-CAATCT (SEQ ID NO: 7) (REVERSE). The PCR (35 Cycles) conditions were 94° C. for 20 Sec, 50° C. for 30 Sec, and 72° C. for 60 Sec. The amplified 3.3 kb DNA was cloned into p CAT3 Promoter vector (Promega) as a Kpn I fragment using standard cloning procedures. This construct will be referred to as pMS 26. DNA binding sequences in the upstream genomic DNA. Furthermore, we have also shown that 3.3 kb of upstream DNA can drive the expression of CAT gene in a myogenic precursor cells lines. As shown in FIG. 1 the isolated upstream sequence has consensus sequences for a typical eukaryotic basal promoter comprising 'CAT' Box and 'TATA' box sequence (Cohen et al 1986, Wingender 1988). A consensus for CAT box (CAAATG) is centered at −206 bp where as consensuses for two TATA boxes are centered at −139 and −163 bp respectively which binds the well characterized basal transcription factor TBP (TATA box Binding Protein), an early step in the formation of pre-initiation complex (Kambadur et al., 1990) of RNA polymerase II mediated transcription. In addition, we have also discovered several 'E' boxes in the upstream sequences of myostatin (Lassar et al 1989). E box has been shown to bind to the basic helix loop helix (bHLH) transcription factors, myogenic regulatory factors like MyoD, Myf-5, MRF-4 and myogenin. These bHLH transcription factors bind to the promoters of several muscle specific genes through bHLH DNA binding domain and control the transcriptional activation of these genes (Rudnicki and Jaenisch, 1995). We have also found a binding site for another muscle specific transcriptional activator MEF-2 (CTAAAAATAAT) at −584 bps in myostatin promoter indicating that myostatin gene regulation may occur by several independent muscle specific transcription factors (Gossett et al 1989).

3. Transfections and CAT ELISA

Four micrograms of CMV-CAT (positive control), p CAT promoter (negative control) and pMS 26 vectors were transfected into actively growing C2C12 myoblast cultures using Fugene 6 (Roche Diagnostics) according to the manufacturers protocol. Twenty four hours after the transfection the C2C12 cells were made to differentiate in low serum medium for a period of forty eight hours. The cells were subsequently washed and amount of CAT protein in the cell extract was measured using a CAT ELISA kit (Roche Diagnostics) according to the manufacturer's protocol.

Results 3.3 kb of Upstream Sequences Harbours Myostatin Enhancer Sequences

In order to identify the enhancer sequences that drive myostatin expression in a myogenic cell, a reporter CAT construct was made with the 3.3 kb of upstream genomic DNA (pMS 26) and transfected into C2C12 myoblast cell line. The pCAT promoter vector and CMV CAT constructs were used as negative and positive controls respectively in this assay. When cell lysate from transfected C2C12 myoblasts were assayed for CAT protein by ELISA, it was observed that the cells transfected with myostatin promoter construct (pMS 26) had a CAT content of 250 picograms/ml (FIG. 2). Whereas in the cells transfected with a negative control vector (p CAT promoter vector) CAT protein content was 5 picograms/ml (FIG. 2).

Discussion

Transcriptional regulation plays a crucial role in determining patterns of tissue specific gene expression during development and differentiation. During the early embryonic myogenesis, several transcription factors like MRFs (MyoD, Myogenin, Myf-5 and MRF-5), Pax-3 control the determination, proliferation and the differentiation of myogenic precursor cells (myoblasts) by positively regulating the transcription of muscle specific genes (Rudnicki and Jaenisch, 1995). Myostatin, a gene which is shown to negatively regulate the growth of muscle, is expressed early in embryonic myogenesis in somites and the expression is continued in adult axial and paraxial muscle (Kambadur et al., 1997). Furthermore, it is also shown that myostatin gene expression is differentially regulated in different axial and paraxial muscle (Kambadur et al., 1997). Here, we have isolated the upstream sequence of myostatin gene and have characterised the several muscle specific DNA binding sequences in the upstream genomic DNA. Furthermore, we have also shown that 3.3 kb of upstream DNA can drive the expression of CAT gene in a myogenic precursor cells lines. The isolated upstream sequence has consensus sequences for a typical eukaryotic basal promoter comprising 'CAT' Box and 'TATA' box sequence (Cohen et al 1986, Wingender 1988). A consensus for CAT box (CAAATG) is centered at −206 bp where as consensuses for two TATA boxes are centered at −139 and −163 bp respectively which binds the well characterised basal transcription factor TBP (TATA box Binding Protein), an early step in the formation of pre-initiation complex (Kambadur et al., 1990) of RNA polymerase II mediated transcription. In addition, we have also discovered several 'E' boxes in the upstream sequences of myostatin (Lassar et al 1989). E box has been shown to bind to the basic helix loop helix (bHLH) transcription factors, myogenic regulatory factors like MyoD, Myf-5, MRF-4 and myogenin. These bHLH transcription factors bind to the promoters of several muscle specific genes through bHLH DNA binding domain and control the transcriptional activation of these genes (Rudnicki and Jaenisch, 1995). We have also found a binding site for another muscle specific transcriptional activator MEF-2 (CTAAAAATAAT) (nucleotides 9819–9829 of SEQ ID NO:1) at −584 bps in myostatin promoter indicating that myostatin gene regulation may occur by several independent muscle specific transcription factors (Gossett et al 1989).

CONCLUSION

A genomic clone containing 10.0 kb of upstream regulatory sequence of myostatin is isolated for the first time.

The enhancer sequences of the myostatin gene have been characterised.

Several E boxes and one MEF-3 binding site that are specifically observed in muscle specific enhancer sequences are also seen in myostatin enhancer sequences.

It will be appreciated that it is not intended to limit the invention to the aforementioned examples only, many variations, such as might readily occur to a person skilled in the art, being possible without departure from the scope thereof as defined in the accompanying claims.

REFERENCES

[1] Wingender E. (1988) Nucleic Acids Res. 16, 1879–1902.
[2] Cohen R. B. et al (1986) Mol. Cell. Biol. 6, 821–832.
[3] Lassar B A. et al (1989) Cell 58, 823–831.
[4] Gossett L. A. et al (1989) Mol. Cell. Biol. 9, 5022–5033.
[5] Pang K. M. and Knecht D. A. (1977) Biotechnologies 22:1046–1048
[6] Rudnicki M. A. and Jaenisch R. (1995). BioEssays. 17 3 203–209
[7] Kambadur R. et al. (1990) Proc. Natl. Acad. Sci 87 9168–9172
[8] Kambadur R et al (1997) Genome Research 7: 910–915

All of the above listed documents are incorporated into the present specification in their entirety by reference.

The invention claimed is:

1. An isolated DNA molecule comprising the polynucleotide sequence of SEQ ID NO: 1.

2. An isolated DNA molecule selected from the group consisting of:
   a) a DNA molecule that is at least 75% identical to a DNA molecule consisting of SEQ ID NO:1; and
   b) a DNA molecule that hybridizes under stringent conditions to the DNA molecule of a),
   wherein the isolated DNA molecule is able to drive expression of a heterologous gene operably linked thereto.

3. An isolated promoter sequence comprising a polynucleotide sequence having at least 75% identity to the polynucleotide sequence of SEQ ID NO:1 which drives expression of a heterologous gene operably linked thereto.

4. An isolated promoter sequence as claimed in claim 3, wherein said promoter sequence is tissue specific.

5. An isolated promoter sequence as claimed in claim 4, wherein said promoter sequence is specific for driving expression in muscle cells.

6. An isolated promoter sequence as claimed in claim 3 comprising the bovine myostatin promoter.

7. A recombinant cloning vector comprising the DNA molecule as claimed in claim 1.

8. A host cell transformed or transfected with the recombinant cloning vector as claimed in claim 7.

9. A recombinant DNA construct comprising the promoter sequence of claim 3, operably linked to a coding sequence of a gene of interest.

10. A recombinant DNA construct as claimed in claim 9 wherein the gene of interest is selected from the group consisting of myogenic regulatory factors, myostatin and myostatin receptors, oncogenes, genes that regulate muscle growth and differentiation, muscular dystrophy, and any other gene expressed in muscle.

11. A vector containing the DNA construct as claimed in claim 9.

12. A host cell transformed or transfected with the vector as claimed in claim 11.

13. A method of cloning the DNA molecule as claimed in claim 1 comprising the steps:
   a) inserting the isolated DNA molecule into a suitable replicable cloning vector;
   b) transforming or transfecting a host cell with said vector in vitro;
   c) culturing host cells; and
   d) isolating a cloned DNA molecule.

14. An isolated promoter sequence as claimed in claim 3, which comprises the sequence from nucleotides 7103 to 10402 of SEQ ID NO:1.

* * * * *

SEQUENCE LISTING

<160> NUMBER OF SEQ ID NOS: 7

<210> SEQ ID NO 1
<211> LENGTH: 10492
<212> TYPE: DNA
<213> ORGANISM: Bovine

<400> SEQUENCE: 1

```
gaattcttct atggctatca ccatgtccaa aacactacct gagtaaagaa ggagtcattt      60
ttttttttaag ggtttaaaaa atttaaaaat ttttaaatta aatttaaaat tgaaatctaa    120
aaaaatttta agaaaaattt tttttaatct gcagaaacat actctgtatt gagtctatgg    180
ttaccaaaga tcccccaga acaaaacccc aagaattgca agattttctc ttgggaagtg     240
tttgtttact ggaaggctta ttaactcaat aataagggag agtaaagact tcaaaactaa    300
agatctgttt ttgtcagttc aatctatatt gtcatctgct ctggaaaccc tgagcttgtt    360
ctaaagtaaa ctgaactatc atgaagaaaa tcagccatca aaatagtgaa acgaacctc     420
ttacactcag ttttttctca tttgtaaatt taaaaaattt aacttcatta agtctgggga    480
ccaatgtata gctgcaagca ggaattttat gccttcttaa tccagagagg tgggcaatgg    540
tgtgggttta gaccagaagt aaggatgtgg gtgcagcaaa tatgacagcc caactgctgc    600
tgctgctgct aagtcacttc agtcgtgtcc gactctgtgt gaccccagag acggcagccc    660
accaggctcc cccgtccctg ggattctcca ggcaagaaca ctggagtggg ttgccatttc    720
cttctccaat gcatgaaagt gaaaagtgaa agtgaagtcg ctcagtcgtg tccgacccct    780
agtgaccca tggactgcag cctaccaggc ttctccgtcc atgggatttt ccaggcaaga    840
gtactggagt ggggtgccat tgccttctcc atgacagccc aactagagac tgctataact    900
tatatcagag aatctgaaac tccctacagg ctatcttgct atatgtgcat tcaacatgaa    960
caaaagaaa attcaagtcc agtaaaaagg gctaaaatag tgaatcacag acttttgcca   1020
aacaacagtc aatgatttgg gcaaaggact taagtagcta tgcttatttg ctattagtag   1080
aataaagaaa tgtttgagcc tggttctcaa tgcttgaata ataagattcc ttttcaagga   1140
aaaacaattt ttttgagaac tcatagataa agtcaaatc tatcacttta gatgtcactt    1200
gaagccaact tgattatagt aaacaaattc agctgtaaac attttttat aacactgtag    1260
acactgtatt tttatacact gtataaatga agacactgaa gatgtaaagt ggtgacctgg   1320
atgatccaga atatgcaata tgcaccaaaa actaagtttt ttaaatgata caaatgaact   1380
tacttacaaa agggaaatag agtcacagat gtagaaaaca tacagttacc taggggacg    1440
gggggagggt aaactgggag ataggaattg acacatacac tctactatat atacactagg   1500
taactaatat gaacctactg tatagcgcac agaactctac ccaatactct gtaatgacat   1560
ttatgggaat agaatccaaa aagagcagat atgtgtatat gtataaactg attcacaccc   1620
cttgccttgc ctaaacacac acagacacac acagacacat ccattttgag atttctttcc   1680
tcctctttgg ctacttttga ctcagtttga cctagatagg acctgtgctg ggtaagggct   1740
ttggcagtct taagtagtgt cagagcaagc acagtcactc cctagcaagg tcttattact   1800
agctacagag tctctctgtg cagtcataga tcactgagtg caaagtcca gtgcaatgtt    1860
tgagtcccat gcatgctctc acagaactga gagggaggc aaggacacag gaccctccag    1920
tgctgggact ctctactggg gtgagcaaga gggaacccaa tagaaatgct gcgaaccaca   1980
gagccactca gaaagcctgt aaatataaac ataacaacac attatgaata tataagtata   2040
```

-continued

```
agtataccta ccaaaaaatc agaaagttga acttttttgt attcaaggga acagtcattc    2100
atttatcggt tcagttatca gtaaacacat ttgggaactg taaaaatcta atcagttcag    2160
ttcagttcag tcgctcagtc gtgtctcttt gcgactccat gaatcgcagc acgccaggcc    2220
tccctgtcta tcaccaactc ccggcgttca ctcagactta cgtccatcga gtcagtgatg    2280
ccatccagcc atctcatcct ctgtcgtccc cttctcctcc tgcccccaat ccctcccagc    2340
atcagagtct tttccaatga gtcaactctt ctcacgaggt ggccaaagta ccaagtcttt    2400
gagtctagtc tctttttca atggagaaga agaggaaacc aaattataac ttaattttta    2460
ttctttgtat tacaagtgta taattaatac actggagttt ccatttcaga aggaagaag    2520 agaaatcaca ttttgcagct ttcctgaact aatacaaaga aatgcagaag ttttgttaac    2580
tgggatatta ttatgacacg ttgccataat atgaatgtca tcatctcaag actgacctga    2640
aaaccaaaat aaaaaaaaaa agagagagag agagagagag agagaaaaaa aagaaaaccc    2700
tccagaccag atttcagtct accacttgag ctgacaaaca ttggccaaat gtcctctaca    2760
gaacctgtaa gttagtagtt ggtaattata aacaataaaa gtatatattt ctgctcctgg    2820
caataattat gtatcagtta aaagtatac attgtctaaa aaatcaccat atttgatgtc    2880
tcattaaaac aaagttacaa atattaagat gagaggactt aaagttagat gggaaaatat    2940
tcaattgaag cagtataaaa tgcattactc tggggcaaag tgtggtctgg agatccctgg    3000
agtgaagacc cttttagaca atctgtggag taagaactgt tttcataaca aagctaagat    3060
ttccttgcta ttctcatttt ctcttacgta tatagtcgag ttttccagaa gttccatgtt    3120
atgtaacatc atcattactc tgtcagcaaa tagaatacat gtttgcatat gtctatattc    3180
taacatttct catttttaat ttataattca ttaaatattg atagatatga cccacataaa    3240
caaaagcttt tcaggatcct gaataacttt tcagagtaaa ggaatcttga gaccaaaagg    3300
tttgagaatt actgttttag gggatacacc tcaagtgaaa gagcacgcct catcacattt    3360
ccactctata tggaagaatc tagaagattg aacctataat tgaagagtgc aggctttatg    3420
aagacagtga ctgtttctgt ctgctttctc ctcagaattt agcatgatgc caggcacata    3480
atttgttgtt gttcagctgc taagtcatct ctgactttt gcaaccccat gaactgcatg    3540
caacatgcca ggtttctctg cttttcactat ctcctggagt ttgctccaac tcatgtccat    3600
tgagtcactg ataccatcca acgatctcat cctctataag acacattata gacattagaa    3660 tatttttcata aaataataag tgaattaata cagctgaaac tcaaacagca tagggggttac    3720 aagtaccaac tcgcgtccaa gttgaaaatc cacatataat cttaaggtca gccttggata    3780
catgcatatc caaggtttccc catctgagga ttcaaccaac ctcagatagt gtagtactgc    3840
agtacacatt tagtgaaaaa tgtgcatata agtggaccca tgcaggtcaa acctgcgttt    3900
tccaagggtc cacagtacac acacacatgc atacatgcat ctctaaatga agctttgcc    3960 atctgactta ctcaaggtca cataaaacgt cagcgagaaa cccagaacta tattccagat    4020
ctctgttcct atactgttac tccctgagtc aagggtactt tgttttttgt tcattttat    4080 tctgtaatct attgagatca cagataatca gatgttgcca ctgtaggatg gcagcctctc    4140
atgctgttat gtgaattgag cactatccag tttgtttctg gctttaagtg taatcagaac    4200
agtgttatat caaagggcta tcatcacaag gaaatggcaa gagtgatcag ataaaatgca    4260
tctttctctc ttttcccaca acagactcga attttcatg attcatcctt attctaattc    4320
ttcagttcag ttcagttcag tccttcagtc atgtccaact ctttgccacc ccatgaatct    4380
```

-continued

```
cagcaagcca ggcctccctg gtccatcacc aactcccaga gttcacccag actcacgtcc    4440
atcgagtcag tgatgccatc tagccatctc atcctctgtc gtccccttct cttcctgccc    4500
ccaatccctc ccagcatcag agtcttttcc aatgagtcaa cttttcacat gaggtggcca    4560
aagtactgga gtttcagctt tagcatcatt ccttccaaag aaatcccagg gctgatctcc    4620
ttcagaatgg actggttgga tctccttgca gtccaaggga ctctcaagag tcttctccaa    4680
caccacagtt caaaagcatc aattcttcgg cgctcagctt tcttcacagt ccaactctca    4740
catccataca tgaccacagg aaaaaccata gccttgacta gatggaccct tgttggcaaa    4800
gtaatgtctc tgcttttcaa tatgctatct aggttggtca taactttcct tccaaggagt    4860
aagcatcttt taatttcatg gctgcagtca ccatttgtag tgattttgga gcccagaaaa    4920
ataaagtctt gacactgttt ccactgtttc cccatccttat ttcccatgca gtgatgggac    4980
cggatgccat gatcttagtt ttctgaatgt tgagctttaa gccaactttt tcaatctcct    5040
cttttcacttt catcaagagg cttttgagtt cctcttcact ttctgccata agggtggtgt    5100
catctgcata tctgaggtta ttaatatttc tcccggcaat cttgattcca gcttgtgctt    5160
cttccagccc agtgtttctc atgatgtact ctgcatagaa gttaaataag cagggtgaca    5220
atatacagtc ttgacatcct ccttttccta tttggaacca gtctgttgtt ccatgtccag    5280
ttctaactgt tgcttcctga cctgcataca ggtttctcaa gaggcaggtc aggtggcagg    5340
tcaggtggtc aggaacatct ctttcagaat ttttgacagt ttattgtgat ccacacagtc    5400
aaaggctttg gcatagtcaa taaagcagaa atagatgttt ttctggaact ctcttgcttt    5460
ttcgatgatc cagcagatgt tggcaatttg atctctggtt cctctgcctt ttctaaaacc    5520
agcttgaaca tcaggaagtt catggttcac gtattgctga agcctggctt ggagaattta    5580
gagcattact ttactagcat tacttttcac aataaactgt ggaaaattct gaaagagatg    5640
ggcataccag accaccggat ctgcctcttg agaaatttgc atgcaggtca ggaagcaaca    5700
attagaagtg gacatggaac aacagactgg ttccaaatag gaaaaggtgt tcgtcaaggc    5760
tgtatattgt caccctgttt atttaacttc tatgcagagt acatcatgag aaacgctggg    5820
ctggaagaag cacaagctgg aatcaagatt tccgggagaa atatcaataa cctcagatat    5880
gcagatgaca ccacccttat ggcagaaagt gcagaggaac taaaaagccc cttgatgaaa    5940
gtgaaagtgg agagtgaaaa agttggctta aatctcaaca ttcagaaaac gaagatcatg    6000
gcatccggtc ccatcacttc atgggaaata gatgggaaa cagtggaaac agtgtcagac    6060
tttattttc tgggctccaa aatcactaca aatggtgact gcagccatga aattaaaaga    6120
tgcttactcc ttggaaggaa agttatgacc aacctagata gcatattgaa aagcagagac    6180
attactttgc taacaaaggt ccatctagtc aaggctatgg ttttcctgt ggtcatgtat    6240
ggatgtgaga gttggactgt gaagaaagct gagtgccgaa gaattgatgc ttttgaactg    6300
tggtgttgga gaagactctt gagagtccct tggactgcaa ggagatccaa ccagtccatt    6360
ctgaaggaga tcagccctgg gatttctttg gaaggaatga tgctaaagct gaaactccag    6420
tactttggcc acctcatgtg aagagctgac tcattggaaa agactctgat gctgggaggg    6480
attggggggca ggaggagaag ggggcgacag aggatgagat ggctggatgg catcactgac    6540
tcaatggacg tgagtctgtg tgaactctgg gagttggtga tggacaggga ggcctggcgt    6600
gctttgattc atgggtcac aaagagtcgg acacgactga gcgactgatc tgtctctctc    6660
ttactagcat gtgtctcctc ctttttttgc cacatcatca aactcctggc aaacttcaca    6720
ttaataacat ttgggagctt ccagaatgca aacagtgaaa ccattaatgt ttttgggaa    6780
```

```
atatgcttta tactctcaat gttgttttga aacgcacacc ccctcccctg ccgcctggtg    6840
tttgtaagac agttgagaga agtttgcttg ctaccttact tatggttaca caaacgtaag    6900 gcccctgag tacaaagaag aacaggggga acgcaaactt caggcccgt gaggaggggc      6960 actggactcc tgtgagaaga aactgctttc aaagaattcc tgggagaaat tctctatgca    7020
ctcatcctag caacaaagtc ctgtccgaag ttaggcccgc agcacccaca cggcagtgaa    7080
ggttcctact gctggtgaac cttgctgctc cgaagccata ggaaggttgc aaatcccggc    7140
actggagaag gaaaacacgt tcttgaaatt tcttgagtac ctcttaattc attcaatgct    7200
gacctccgga gattggatag agctgactct cattattcac agtggttatg ttctacccaa    7260
tcactgccaa catgaataag tgattcctga accactgccc ctaggggaac tacaaggtta    7320
gattcccgtc agcctctggt cacgttttg ttaaccaatc aataaataac cttgttttgt     7380
gtgcatttct gttttaaaat atctttattt aatacgtact gctaattctt caacatttgg    7440
ttcacaacca aaaggcccta ttaactggaa gccctgaatg aagcttacat aacacacatt    7500 gttttttctat gaggaaaaat ttttccttca gtcctgccac agccttcttg cttaaaattg    7560
tggacaaaat atacataaca tgaaactgac tattatttaa ctgattttaa ctgtacagtt    7620
cagtggcatt aagtacactt accttgctgt ggaactatga tcaacattca tctctagaac    7680
tttttgatct tctcgaattg aaaactctgc atctattgca cagtagcttt cccccatcac    7740
accgcaccct tcctccagcc cccggcacc accatccttc tttccatgac agtcatcctg      7800
tgcctaggaa cacagccctt caacactacg cttgggggc actgtaagca acaggatcac     7860
tccctaccgc caccaaatgc acacaaaaat ataaaaagca tggtggcata tcgattgcaa    7920 aaaggggtgct tgctaagtat gagggctgaa acaaggcaga gaattgacta ggttgacctc    7980
agctgggatc ctgtgtgttg gaagcctcaa attttccatt gttctgtgca tacgcacaaa    8040
tgcttataaa agcactgtaa ggattgatta tgaagttaag ataaatctca gcaagacata    8100
aatgtgcaag cacgggatcc atgaataacg agcactgacc atgtggaaat gataatcttt    8160 gtttcctta ttccaggcag taaggagaaa gcgctcacag ggctgcctta caccatttta      8220
ctagagagct agcctatgtc agtcggtagc tgcaattac aaactgaagc agttctagtt      8280
catgtggagg atgaatttaa ccataatctc aacccctct gcatgaaaca gagactaagt      8340
actcaagtac cagttatcag tcacttacta tatgacaggc actgtactca acaatttaca    8400
tgtattattg aattacatgc ccccaacact ctatgaggaa gctgaaggtt agagaagtat    8460
ctcattcatt attacacagt ggcaaactga gatctgaact caggtctatc caactccagg    8520
acctgagatc ccaattgcta cacaattcta atcaagttaa aagggaaaaa ggatttgatt    8580
tgctcagaag tgtatagggg catatgttac aattataaca ttacaaagat ttatatgttg    8640
aaaaataaat ttatcaaaca aataaaaactt tataagcctg atctaatact gctccgcaac    8700
aaagactatc tgaaatcctt cagggcatct ggtttgtgtc tggttttcct taatctttaa    8760
tgatgggcaa atctaatgca ttatgtaagg ccattttttc tcaagagatg tagataccte    8820 ttaagaattt gatgaaaatg cattaacttt tcaggctact gagttgcatt ttagtgcact    8880
gaggcagtaa attagtgtac aatgtgcgaa agtagtgacc taaaaataa atatttgata    8940 tgaaccactg cactctcttg gggaaaaaag taatggatta actctcttag gagtccttag    9000
cttccccaaa agtagtagga aaataaatc tcctgtggcc tggaaacagc ttctgttct     9060 tgctggctat atttgtttag gttttaata gttcatttga ttagaccttg tggctcccaa    9120
```

-continued

```
agctaaggtt gagagtttga tccctacaga ggccacttca atttagagaa caaaaagccc   9180
cattctctgc tcccagacct tacccccaaat ccctgccagg tgtctgccct ccggtcaaat   9240
gagaaactgg caaaggaagt actaggaggt cgcacagtac taggaagtag aaaaatggac   9300
tagcacacta ctgagaagca gaaaaatggg caccttcat gatggtgttc ctttccttt    9360 ctgtgttcac aatgctccga tataatttac agagggtaga taactacatt tttttctttt   9420
accactggaa ggctgaggaa actttgtta cccatcataa aattcactat cttctaagtc    9480
attctatgtt attctaagat caaatagctg acaatatcct ctttgtaata aacaatgaaa   9540
aaacacatcc tctgagcaat attaatctgc aactttagga taggaagtaa cttaatacta   9600
gtcaattgaa actgaaatac aattttcata tgaataaaag atattattta aaagtaattc   9660
catgagcaat ttaatattaa agtaggattt tcattatgtg ttaagaattt attcagggaa   9720
acaagtttct caaattatag cagaaaatct tttactagta tcacagtctt ttcatttaag   9780
tcttcctgaa taaatctgta ttttctaatt atacaagact aaaaataatt taatataaca   9840
aataaaatta ttttttacttc aaatgcttac ttaaatagta taaaatcatt ttattttctg   9900
agggaaaagc atatcaactt tttaagtatg aagtgtaaat taagatttat tcacttaaat   9960
tataattttt aaagtttcac atataaagat gaataagatc taagtgtata tgttattgtt   10020
aataaagttt taattttttc gcatgtcaca tacagccttt attattcata gatttattcc   10080
ttttaagaag tagtcaaatg aatcagctca cccttgactg taacaaaata ctgtttggtg   10140
acttgtgaca gacagggttt taacctctga cagcgagatt cattgtggag caagagccaa   10200
tcacagatcc cgacgacact tgtctcatca aagttggaat ataaaagcc acttggaata    10260 cagtataaaa gattcactgg tgtggcaagt tgtctctcag actgggcagg cattaacgtt   10320
tggcttggcg ttactcaaaa gcaaaagaaa agtaaaagga agaagtaaga acaagggaaa   10380
agattgtatt gattttaaaa ccatgcaaaa actgcaaatc tctgttata tttacctatt     10440 tatgctgatt gttgctggcc cagtggatct gaatgagaac agcgagcaga ag           10492
```

<210> SEQ ID NO 2
<211> LENGTH: 24
<212> TYPE: DNA
<213> ORGANISM: Made in the lab

<400> SEQUENCE: 2

```
ctgctcgctg ttctcattca gatc                                           24
```

<210> SEQ ID NO 3
<211> LENGTH: 23
<212> TYPE: DNA
<213> ORGANISM: Made in the lab

<400> SEQUENCE: 3

```
atcctcagta aacttcgcct gga                                            23
```

<210> SEQ ID NO 4
<211> LENGTH: 18
<212> TYPE: DNA
<213> ORGANISM: Made in the lab

<400> SEQUENCE: 4

```
ggctgtatgt gacatgcg                                                  18
```

<210> SEQ ID NO 5
<211> LENGTH: 20

-continued

```
<212> TYPE: DNA
<213> ORGANISM: Made in the lab

<400> SEQUENCE: 5
tgaaccactg cactctcttg                                               20

<210> SEQ ID NO 6
<211> LENGTH: 32
<212> TYPE: DNA
<213> ORGANISM: Made in the lab

<400> SEQUENCE: 6
ggggtacccc aattcctggg acaaattctc ta                                 32

<210> SEQ ID NO 7
<211> LENGTH: 30
<212> TYPE: DNA
<213> ORGANISM: Made in the lab

<400> SEQUENCE: 7
ggggtaccgg ttttaaaatc aatacaatct                                    30
```